United States Patent [19]

Bryan et al.

[11] Patent Number: 4,961,163

[45] Date of Patent: Oct. 2, 1990

[54] SYSTEM FOR MONITORING AND REPORTING THE OPERABILITY AND CALIBRATION STATUS OF A PH SENSOR

[76] Inventors: Avron I. Bryan, 26 Country Club Rd., Cocoa Beach, Fla. 32931; Michael R. Cushman, 521 Brandonwood Rd., Kingsport, Tenn. 37660

[21] Appl. No.: 279,574

[22] Filed: Dec. 2, 1988

[51] Int. Cl.$^5$ .................... G06F 15/46; G01N 27/26
[52] U.S. Cl. .................. 364/550; 204/401; 204/412; 204/435; 204/153.21; 364/496; 364/571.01
[58] Field of Search ............ 204/1 T, 401, 403, 408, 204/412, 416, 418, 419, 420, 433, 435; 324/62, 63, 65 R; 364/496, 497, 500, 550, 571.01, 571.02, 571.03, 571.07; 73/1 R

[56] References Cited

U.S. PATENT DOCUMENTS

| | | | |
|---|---|---|---|
| 4,288,308 | 9/1981 | Hach | 204/420 |
| 4,297,193 | 10/1981 | Brezinski et al. | 204/420 |
| 4,447,309 | 5/1984 | Morioka et al. | 204/420 |
| 4,686,011 | 8/1987 | Jäckle | 204/401 |
| 4,777,444 | 10/1988 | Beijk et al. | 204/420 |
| 4,800,513 | 1/1989 | Deutsch | 364/550 |
| 4,822,456 | 4/1989 | Bryan | 204/435 |
| 4,852,385 | 8/1989 | Brinkmann | 204/401 |

*Primary Examiner*—Kevin J. Teska
*Attorney, Agent, or Firm*—Macdonald J. Wiggins

[57] ABSTRACT

In a real time, on-line pH measurement of a process solution, a system provides a continuous data of the physical condition of the pH sensor. The system includes a pH sensor having a glass membrane disposed in the process solution and two electrodes in the solution adjacent the sensor. The two electrodes in the solution are periodically driven by a short time duration dc signal producing a dc current between the two electrodes. This action results in electrolysis ofo the $H_2O$ molecules of the solution at the two electrodes and a resulting decrease in hydrogen ion concentration (a rise in pH value) in the region of the sensor. The sensor response to the increase in pH in the solution is a direct indicator of the complete sensor and system performance and is monitored and analyzed. Visual readouts and threshold alarm circuits are provided which indicate changes in the sensor response to the pH change indicative of a sensor or system degradation or fault.

8 Claims, 1 Drawing Sheet

SYSTEM FOR MONITORING AND REPORTING THE OPERABILITY AND CALIBRATION STATUS OF A PH SENSOR

FIELD OF THE INVENTION

The present invention relates to a pH monitoring system for a solution containing water, and more particularly to a system including monitoring of the physical condition of a pH sensor of the system.

DESCRIPTION OF THE PRIOR ART

The pH of processes containing water is important in many industrial processes and is critical for processes based on microorganisms; for example, fermentation, recombinant DNA processes, and waste water treatment. The present real time measurement of pH in industrial processes normally utilizes the glass pH electrode. The pH signal developed by the sensor is in response to the concentration of hydrogen ions in the solution. Specifically, the glass electrode is immersed in the process solution and the difference in hydrogen ion concentration on the inside and outside of the pH sensitive glass generates a potential proportional to the process hydrogen in concentration. The operation of the sensor is maintained at a state in which the signal from the sensor is proportional to the hydrogen in concentration in the sample.

There are a number of problems that can occur with this measurement system. For example, the glass membrane can become coated by the process or can change due to structural failure, such as cracks, leakage or degradation. In the sensor body, the physical condition of the electrodes and the condition of the electrolyte directly affect the sensor signal. These problems can occur in prior art systems without being detected resulting in false readings. Such failures can produce significant losses in time and money. There are no systems previously known that continuously detect changes in the sensor glass membrane and that periodically detect performance changes in the sensor or system.

Thus, there is a need for a pH sensor system in which defects in the pH sensor can be detected in real time while a process is on-line, thereby reducing the probability of undetected failures and catastrophic results.

SUMMARY OF THE INVENTION

The present invention is a pH measurement system having a unique real time, on-line capability for continuously monitoring the pH sensor membrane impedance, and for testing the sensor and the system response by generating in the process solution a short temporary controlled change in the hydrogen ion concentration in the vicinity of the sensor. The system then generates reports on relative changes of the sensor response to the controlled periodic change of pH near the sensor in the process solution since the last calibration.

A novel pH sensor is provided having two electrodes external to the body of a standard glass membrane pH sensor. When the system is in use, the pH sensor and the two additional external electrodes are disposed in the process solution or stream. The two additional electrodes function as an anode and a cathode. A small direct current is passed from anode to cathode through the solution for a short period of time. The resulting electrolytic action consumes or neutralizes a small amount of hydrogen ions at the cathode. The cathode is placed such that the change in hydrogen ion concentration will occur in the solution immediately adjacent the sensor glass membrane. The change results in decrease of diffusion of hydrogen ions through the glass which will be sensed by the monitoring system.

The measurement monitoring system is controlled by a computer with appropriate algorithms and additional control hardware to perform all of the functions of pH measurement, testing and analysis of the sensor and system response. To this end, the signal from the pH sensor is applied to an analog-to-digital (A/D) converter and the digitized signals are input to the computer. The computer processes the signals and converts the results to operate numerical read-outs of the pH being measured. When the controlled short change in pH occurs, the rise and decay times of the resulting pulse is measured.

Periodic generation of the short test signal to test and verify the sensor system is provided by a system controlled generator and the two external electrodes. The system, on a programmable periodic basis, applies a low level dc potential between the two external electrodes. The external cathode electrode is placed in close proximity to the pH sensor. The test current results in the electrolysis of the process solution in which the $H_2O$ molecules produce a repeatable quantity of hydrogen and oxygen gases. The production of hydrogen gas consumes hydrogen ions to effectively raise the pH. The increase in pH (over the process solution average pH) is monitored in the normal manner. During the test period of the measurement system, the system pH delivered to users and control systems is maintained at the last average reading before the application of the test signal. The effect of the generated pH change on the sensor is monitored and compared with past behavior stored in the system memory for system check purposes, but is not reported as a change in pH in the solution process.

The system computer, having issued the test signal, can now monitor the pH signal deviation from the normal pH level in the process solution. System computer algorithms then compare the amplitude response, initial speed of response, and decay response to the short applied signal to monitor both sensor and system performance.

It is preferred to include a temperature sensor in the process on-line near the pH sensor. The output of the temperature sensor is converted to digital form which is used by the system computer to thereby compensate the pH sensor concentration readings.

At the time of calibration of the system, the initial temperature and the system response to the test signal are measured and stored. Thereafter, the stored values are used as references to compare against the operational periodic sensor test results. Changes in the glass membrane (after correction for temperature) values indicate degradation or failure of the sensor. Internal sensor electrode degradation or change in electrolyte is indicated by the time and shape of the response to the applied test signal. A failure in some other part of the system is indicated by a lack of response to the applied signal. The measurement system will report on the need for calibration or will produce warnings that the sensor or system has failed or the performance thereof has degraded.

DETAILED DESCRIPTION OF THE PREFERRED EMBODIMENT

Figure 1:
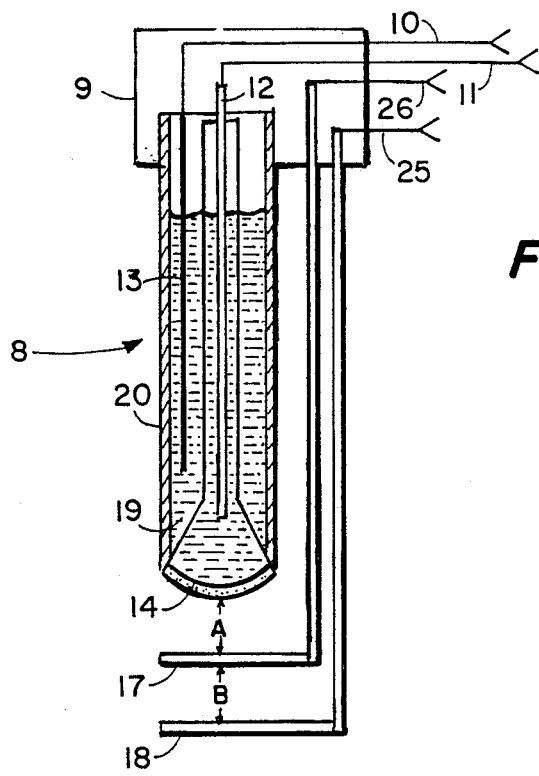
FIG. 1 is a cross sectional view of a pH sensor with external test and monitor electrodes in accordance with the invention.

The invention is a system including monitoring of pH in a process solution and continuous monitoring of the pH sensor. A pH sensor is combined with two test electrodes in the process solution to provide means for testing, analyzing, and reporting the pH sensor status as well as the total system response. Referring to FIG. 1, a standard pH sensor 8 is mounted to a bracket 9 from which monitor and test electrodes 17 and 18 depend. The reference electrode 13 of sensor 8 is preferably silver and is immersed in a saturated silver chloride electrolyte 19. The sensor electrode 12 is preferably formed from silver. Electrodes 13 and 12 are disposed in a housing 20 having an open lower end. A sensor membrane 14 is formed from pH sensitive glass covering the end of housing 20. Test electrode 17 functions as a cathode electrode and is spaced a distance A from glass membrane 14. Test electrode 18 functions as an anode electrode and is spaced a distance B from test electrode 17. Distances A and B are not critical but are normally less than 0.5 inches. Test electrode 17 can be of any suitable cathode material; preferably, test electrode 18 is formed of material that has a low oxygen overpotential such as platinum or lead dioxide.

As will be noted, reference electrode 13 of sensor 8 is connected to lead 10, and sensor electrode 12 connects to lead 11. Test electrode 17 is connected to lead 26, and test electrode 18 connects to lead 25.

Figure 2:
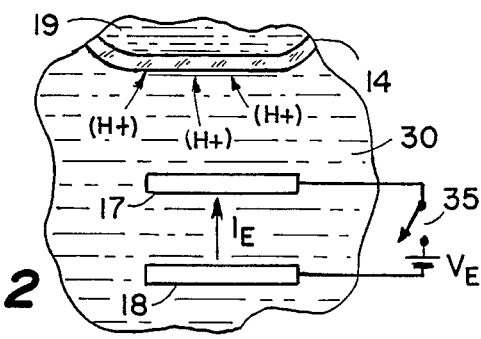
FIG. 2 is a partial view of the sensor and electrodes of FIG. 1 illustrating generation of a pulse for changing the pH for test purposes.

Turning now to FIG. 2, a portion of an operating system is shown with process solution 30. Membrane 14 is indicated with hydrogen ions (H+) incident thereon. The measurement system will normally measure the concentration of such hydrogen ions in solution 30.

Figure 3:
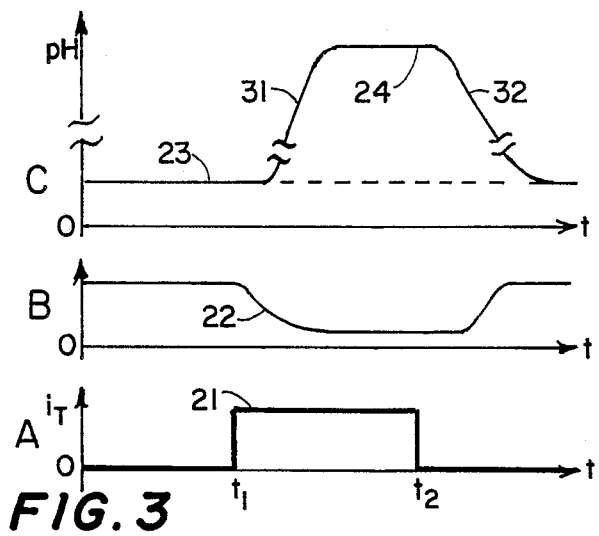
FIG. 3 is a set of pH waveforms produced by generation of the pulse.

The condition of the electrodes 12, 13 of FIG. 1, electrolyte 19 and membrane 14 are monitored by periodically producing a decrease in hydrogen ion concentration directly at the sensor membrane 14. A voltage source $V_E$ and switch means 35 is connected between electrodes 17 and 18. The voltage is applied in a short interval ($t_1$ to $t_2$) as indicated in line A of the waveform diagram of FIG. 3. An electrolysis current $I_E$ will flow, causing electrolysis of the water in solution 30. The hydrogen ions (H+) consumed by the electrolysis will, as indicated in line B, cause a decrease in hydrogen ions as shown in line C. When voltage $V_E$ is turned off at $t_2$, the pH will return to that of the system with a delay time determined by the solution hydrodynamics, buffer capacity, and the like.

When the increase in the measured value of pH from sensor 8 occurs, the increase is analyzed for amplitude 24, rise time 31, and decay time 32. The characteristics of the waveform at calibration are stored and subsequent measurements are compared to the calibration. Any physical changes in sensor 8 will affect the sensor's response to the test pulse and an alarm may be generated if a change is out of preselected thresholds.

Figure 4:
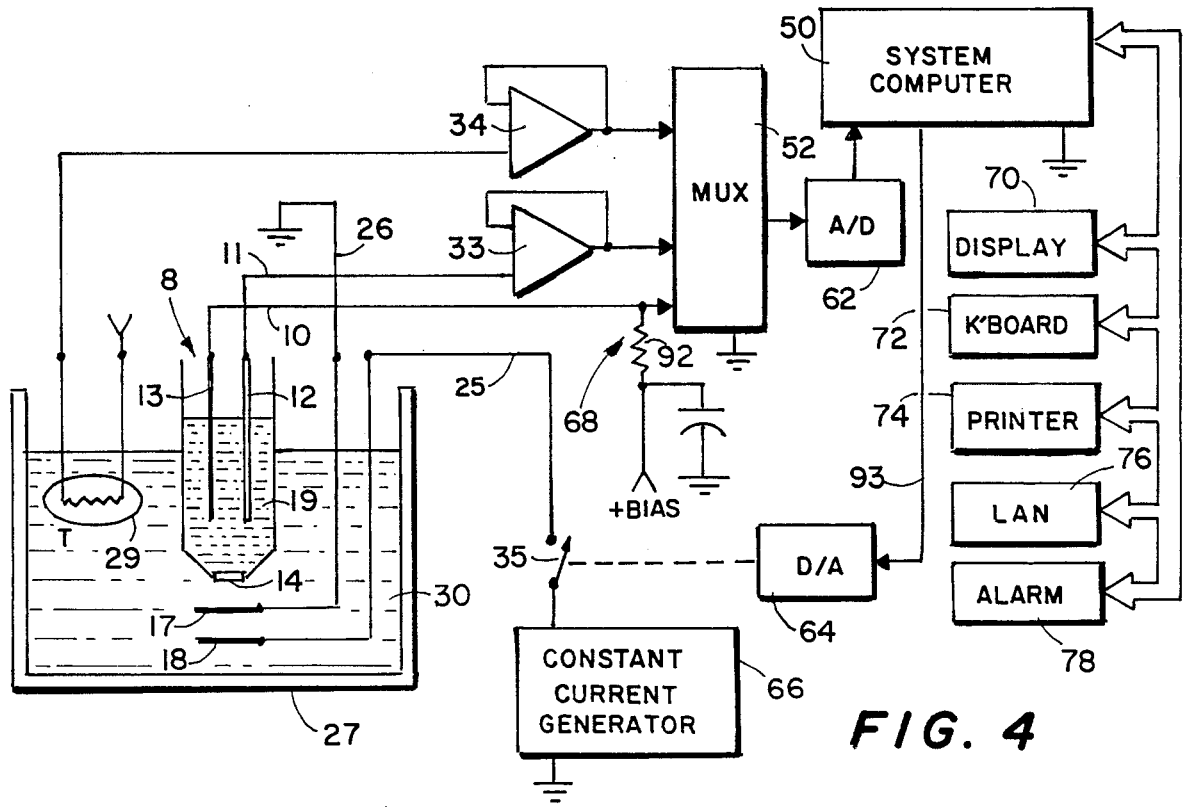
FIG. 4 is a schematic and block diagram of a preferred embodiment of the system of FIG. 4 utilizing a computer for measuring and testing of the sensor with external electrode pulses.

The preferred implementation of the invention is shown by the schematic and block diagram of FIG. 4. A process solution 30 for which the oxygen concentration is to be measured is shown in a tank 27. A pH sensor 8 is shown immersed in the solution 30. In addition, a temperature sensor 29, which may be of any electrical type, is provided to allow automatic temperature compensation of the pH sensor response.

A system computer 50 is provided having a number of stored programs. For monitoring the condition of sensor 8, pulses of increased pH are generated adjacent membrane 14 as discussed above. A stored program in the system computer 50 commands a constant current generator 66 via D/A converter 64 to generate an electrolysis current on a programmable periodic basis. Further, the current amplitude and time duration thereof are programmable to accommodate the process solution characteristics and the locations of the test electrodes 17 and 18. The current to generate the pulse of decreased hydrogen ions is applied via lead 25 to the electrolysis electrode 18 by closure of electronic switch 35 by a command from D/A converter 64. The return path for the current is via test electrode 17, lead 26 and ground.

Having described the test procedure controlled by computer 50, the operation of the system will now be discussed. The sensor electrode 12 dc output is available via lead 11 to the circuit 33 which is connected as an emitter follower circuit. Circuit 33 drives the multiplexer (MUX) 52. Temperature sensor 29 provides a voltage signal via emitter follower 34 to MUX 52. The potential of the bias voltage via bias network 68 on reference electrode lead 10 is connected directly to MUX 52. Multiplexer 52 has its output connected via an analog-to-digital (A/D) converter 62 to system computer 50.

System computer 50 includes stored programs to perform statistical analyses on the data contained in the dc signal from electrode 12. The programs analyze the response of the sensor to the test pulse 22 of FIG. 3, and measure the solution pH. Thresholds for the normal operating parameters of the sensor 8, and the test and monitoring elements of the system, are programmable and are entered into system computer 50. Whenever any of the programmed thresholds is exceeded, an appropriate alarm 78 is actuated. The process solution pH, the sensor response time and decay time to the test signal, and the process temperature are available for real time monitoring on the system display 70, printer 74; a local area network 76; and alarm 78.

Calibration of the system may be carried out by entering appropriate keyboard commands via keyboard 72 or via the local area network 76. The system computer program may select new threshold values for the sensor 8 and system test and monitoring signals based on the calibration.

Although specific illustrations of the preferred embodiment have been presented, these are for exemplary purposes only and various alternative arrangements may be used without departing from the spirit and scope of the invention. In addition, the periodic perturbation of pH in the region of the sensor is applicable to any type of pH sensor, for instance fiber optic based pH probes.

We claim:

1. A test and monitoring system for providing on-line, real-time monitoring of the condition of a pH sensor, said pH sensor having a sensor electrode, a reference electrode, and electrolyte, and a pH-sensitive glass membrane, said sensor immersed in a process solution, comprising:
   (a) a cathode electrode immersed in said process solution adjacent said sensor glass membrane;
   (b) an anode electrode immersed in said process solution and spaced apart from said cathode electrode;
   (c) a source of direct current;
   (d) control means for periodically controlling said direct current source to cause current flow between said anode electrode and said cathode electrode for producing electrolysis in said process solution to thereby decrease the amount of hydrogen ions incident on said sensor, said decrease in hydrogen ions producing an increase in pH relative to the pH due to the process, wherein said pH sensor produces a test signal pulse having a rise time, a maximum magnitude, and a decay time, said pulse superimposed on a process solution pH signal from said pH sensor;
   (e) means for measuring and storing representations of said rise time, said maximum magnitude, and said decay time as calibrated values of said test signal pulse during initial calibration of said system; and
   (f) means for comparing said rise time, said maximum magnitude, and said decay time of said test signal pulse, during operation of said system, with said calibrated values, and for detecting deterioration of said pH sensor when present.

2. The system as recited in claim 1 in which said computer program includes thresholds for said calibrated values, and said system includes means for enabling alarms when a threshold is exceeded.

3. The system as recited in claim 1 which said control means, said measuring and storing means, said comparing means and detecting means includes a system computer.

4. The system as recited in claim 3 in which said control means is an electronic switch connected between said current source, and said cathode and anode electrodes, and said computer includes means for periodically operating said switch.

5. A test and monitoring system for providing on-line, real-time monitoring of the condition of a pH sensor, said sensor having a sensor electrode, a reference electrode, an electrolyte, and a glass membrane, said sensor immersed in a process solution, comprising:
   (a) an electrolysis electrode attached to said pH sensor membrane adjacent said pH sensor glass membrane;
   (b) a test electrode immersed in said process solution and spaced apart from said electrolysis electrode;
   (c) a source of direct current connected to said electrolysis electrode;
   (d) a switch connected between said test electrode and said current source for periodically connecting said electrolysis and test electrodes to said source of direct current for producing electrolysis in said process solution to thereby periodically change the hydrogen ion concentration in the process solution incident on said sensor, said changes producing increases and decreases in pH relative to the pH due to the process solution, wherein said pH sensor produces a test signal pulse superimposed on the pH signal produced by said process solution; and
   (e) a system computer programmed to
      (i) measure and store calibrated values of a rise time, a magnitude, and a decay time of said test signal pulse during an initial calibration of said system,
      (ii) compare a rise time, a magnitude, and a decay time of said test signal pulse during operation of said system with said stored values of rise time, magnitude, and decay time, and
      (iii) detect deviations from said calibrated values indicative of deterioration of said pH sensor.

6. The system as recited in claim 5 in which said switch is an electronic switch, and said computer is programmed to periodically operate said switch.

7. The system as defined in claim 5 in which said system computer is programmed to operate said switch.

8. The system as defined in claim 5 in which said computer includes stored thresholds for each of said calibrated values, and enables alarms when a threshold is exceeded.

* * * * *